US006597804B1

(12) United States Patent
Heuft

(10) Patent No.: US 6,597,804 B1
(45) Date of Patent: *Jul. 22, 2003

(54) METHOD FOR TESTING THE RELIABILITY OF A TESTING APPARATUS ESPECIALLY AN EMPTY BOTTLE INSPECTOR

(75) Inventor: Bernhard Heuft, Burgbrohl (DE)

(73) Assignee: Heuft Systemtechnik GmbH, Burgbrohl (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,913

(22) PCT Filed: Nov. 12, 1997

(86) PCT No.: PCT/EP97/06300

§ 371 (c)(1),
(2), (4) Date: May 7, 1999

(87) PCT Pub. No.: WO98/21566

PCT Pub. Date: May 22, 1998

(30) Foreign Application Priority Data

Nov. 12, 1996 (DE) .......................................... 196 46 694

(51) Int. Cl.$^7$ ................................................. G06K 9/00
(52) U.S. Cl. ....................................... 382/142; 348/127
(58) Field of Search ................................ 382/100, 141,
382/142, 143; 348/125, 127; 250/228; 356/240.1,
239.1, 239.2; 209/524, 526; 73/49.3; 700/121

(56) References Cited

U.S. PATENT DOCUMENTS

| 4,140,901 A | * | 2/1979 | Fischer et al. .......... 250/223 B |
| 4,240,281 A |   | 12/1980 | Lather et al. |
| 4,414,566 A | * | 11/1983 | Peyton et al. ................ 382/142 |
| 4,849,901 A | * | 7/1989 | Shimizu ...................... 700/121 |

FOREIGN PATENT DOCUMENTS

| DE | 2166235 | 7/1973 | .......... G01M/11/06 |
| DE | 3145832 A1 | 9/1982 | .......... G01M/13/00 |
| DE | 4200798 A1 | 7/1983 | .......... G01M/19/00 |
| DE | 3324449 A1 | 1/1985 | .......... G01M/19/00 |
| DE | 4302656 C1 | 5/1994 | .......... G01M/19/00 |
| JP | 01305351 | 12/1989 | ............ G01C/3/06 |
| JP | 03010110 | 1/1991 | .......... G01N/29/04 |
| WO | WO 90/04162 | 4/1990 | ............ G01N/9/04 |

* cited by examiner

Primary Examiner—Samir Ahmed
Assistant Examiner—Vikkram Bali
(74) Attorney, Agent, or Firm—Gardner Carton & Douglas LLC

(57) ABSTRACT

To test the reliability of a testing apparatus which checks multiple objects of the same type for one set feature, generates a feature signal for each object and checks the feature signal with respect to fulfillment of one first set condition, a test object is inserted in the testing apparatus after multiple objects and the feature signal of the test object is checked with respect to the fulfillment of a second condition, the second condition being a feature signal of the test object which corresponds to a previously inputted reference value. The reference value can be inputted by storing the feature signal of a test object as reference value.

1 Claim, 1 Drawing Sheet

METHOD FOR TESTING THE RELIABILITY OF A TESTING APPARATUS ESPECIALLY AN EMPTY BOTTLE INSPECTOR

FIELD OF THE INVENTION

The invention relates to a method for testing the reliability of a testing apparatus which checks a large number of objects of the same type for one feature, generates a feature signal for each object and checks the feature signal for fulfilment of a first condition, a test object being conducted to the testing apparatus after a number of objects and the feature signal of the test object being checked for the fulfilment of a second condition.

BACKGROUND OF THE INVENTION

According to the state of the art, the procedure in reliability tests for testing apparatuses e.g. those for empty drinks bottles, so-called empty bottle inspectors, is that a row of test bottles is prepared so that each contains a certain defect according to the defect recognition specification, i.e. does not fulfil a certain feature. A special test bottle is prepared for every feature checked. The batch of test bottles is then incorporated in the stream of bottles at certain time intervals, e.g. every half hour, or after a certain number of bottles, e.g. 50,000 bottles. This operation can be automatic or manual. The test bottles are marked so that they are instantly recognisable as test bottles. The reliability test consists of checking whether these test bottles can be recognised as defective by the testing apparatus, for example the empty bottle inspector. In the method used up until now, the second condition is thus complementary to the first condition, i.e. the second condition is fulfilled in the test bottles if the test apparatus recognises that the test bottle is defective, i.e. that the first condition is not fulfilled. A record is kept in the testing apparatus. If the reliability test fails, i.e. if one or more of the test bottles is not recognised as defective, the test must be repeated. This is to ensure the operational dependability, i.e. the reliability, of a testing apparatus. This reliability test is unsatisfactory as it is only subsequently recognised that a testing apparatus has no longer functional reliably. The reasons for the failure of a testing apparatus are usually a dirty lens system or a failure of individual components of the recognition electronics.

With the method according to the state of the art, a large number of test bottles had to be used to test the reliability for example of an empty-bottle inspector, every test bottle having a single defect, e.g. a defective closure thread or a foreign body in a single recognition zone. Every type of defect and every recognition zone thus required its own specially prepared test bottle. If a test bottle had revealed several defects, the fact that this bottle was singled out would not have ensured that all the defects were recognized. A set of test bottles therefore consists of e.g. some 10 to 15 bottles.

SUMMARY OF THE INVENTION

The object of the invention is to create a method whereby a deterioration in the operating performance of a testing apparatus can be recognised as early as possible.

According to the invention, this object is achieved in that the second condition is that the feature signal of the test object corresponds to a previously entered reference value.

The idea underlying the method according to the invention that of testing the reliability of the testing apparatus by means of a test object whose feature signal when the test apparatus operates correctly is very precisely known and is entered in the testing apparatus as a reference value. Apart from unavoidable inaccuracies when checking the test object, the feature signal must correspond exactly to the reference value. It does not matter whether the feature signal fulfils the first condition, i.e. whether the test object is free from defects.

For non-defective objects, the feature signal can lie within a larger range or above or below a threshold value.

The method according to the invention is suitable in particular for testing the reliability of empty bottle inspectors.

A procedure frequently used with empty-bottle inspectors when checking on the absence of foreign bodies in that an image of the object is scanned pointwise e.g. by means of a CCD camera, generally in two directions at right angles to each other, and the brightness of each image point is ascertained and light-dark and dark-light transitions recorded by comparison with the brightness of adjoining image points. Such a transition always occurs e.g. if the scan passes over the edge of a foreign body in an empty bottle. Even empty bottles which are free from foreign bodies have a certain number of brightness transitions, e.g. up to 100 brightness transitions, due to uneven areas in the receptacle wall or the fluting on the edge of the base. A single object counts in this case as free from foreign bodies up to 100 brightness transitions, i.e. a feature signal of 100 still satisfies the first condition.

During proper operation e.g. of an empty bottle inspector, a feature signal is obtained for the predominant majority of the empty bottles e.g. 90%, which is somewhat below the number of 100 light-dark transitions. If the sensitivity of the recognition device of the testing apparatus drops due to dirt or other reasons, this tends to lead to a decrease in the number of light-dark transitions recognised per empty bottle. If the reference value of a test bottle is e.g. 95, the feature signal of the test bottle falls with a decline in the sensitivity of the recognition device. Depending on how large the deviation from the reference value is, various measures can be taken. For a deviation of 10% e.g. a warning signal can simply be given out, while for a deviation of 20% or more the testing apparatus and the entire transport apparatus can be stopped.

A particularly advantageous version of the method according to the invention results in conjunction with defect recognition methods in which not only the number of light-dark transitions are counted, but also the light-dark contrast of the brightness transitions is established. The found image elements deviating from the background are divided into e.g. eight different brightness classes or the light-dark transitions are divided into e.g. eight different contrast groups, the number of light-dark transitions being counted only after this classification and being compared within each class with a special threshold value. If the recognition device of the testing apparatus is dirty, a light scatter appears on the lenses or the glass protection disks, which leads to a decrease in the light-dark contrast, as a misty-like blurring effect covers the image scanned by the recognition device because of the light scatter. The reduction in the light-dark contrast causes a shift in the light-dark transition within the contrast classes, in such a way that the feature signals more frequently fall in the classes with less contrast. When testing the reliability of the testing apparatus, there is now no need to rely just on the comparison of the number of light-dark transitions, but a comparison is carried out with a threshold value in every one of the contrast classes and, in addition, the distribution of the feature signals over the individual contrast classes can be taken into account.

Assuming that a test bottle has 100 light-dark transitions of the order of 250 shades of grey, and two contrast classes are used, the first contrast class containing light-dark transitions with under 180 shades of grey and the second contrast class containing light-dark transitions with over 180 shades of grey: if the lens system of the recognition device is slightly dirty, then 100 light-dark transitions are still recorded, but with diminished contrast, e.g. only 150 shades of grey. The established feature signal then reads "100 light-dark transitions in the second contrast class" and thus does not correspond to the reference value which reads "100 light-dark transitions in contrast class 1". The deterioration in the possibility of defect recognition by the recognition device thus becomes noticeable by shifting the light-dark transitions from contrast class 1 into contrast class 2. Through this version of the method according to the invention, statements can be made about the reliability of the recognition of in particular small defects or defects in the form of transparent foreign bodies.

With this version of the method according to the invention, the feature signal thus not only contains details of the number of light-dark transitions but also details of the distribution of the light-dark transitions over the different contrast classes. Corresponding details are also contained in the reference value. A particularly early recognition of the reduction in the sensitivity of the recognition device is thereby possible. A dirtying of the lens (system) of the recognition device does not lead firstly e.g. to change in the amount of light-dark transitions, but certainly leads to a change in the distribution of the light-dark transitions among the different contrast classes.

The setting of the reference values for a testing apparatus can be carried out manually, e.g. using a keyboard, or by means of the test objects themselves, the test object being sent through testing apparatus and the feature signal ascertained being stored as a reference value. The percentage reproducibility of the reference value can also be determined, and the maximum permissible deviation of the test signal above or below the reference value at which the second condition can still be seen as fulfilled thereby established, by means of further passes of the test object through the testing apparatus.

The method according to the invention is of importance in particular in the food industry as it is particularly important here that testing apparatuses operate error-free and that a reduction in the reliability of a testing apparatus is already recognised before defective bottles e.g. those bottles still containing caustic solution residues, pass testing apparatuses unrecognised. It is just as important that there are no foreign bodies such as dirt or cellophane films in empty bottles, that the internal pressure is not too high and not too low, that the bottle opening has no splinters and, in the case of cans, that they are in a satisfactory state before filling and that they are properly sealed.

The recognition procedure already described, in which the number and optionally the contrast of the light-dark transitions is determined, is suitable in particular for recognizing foreign bodies in empty bottles and for recognizing splinters in the mouth opening. Absorbent foreign bodies, e.g. dirt, are established by the bright-field method while transparent foreign bodies, e.g. films, are detected by the dark-field method (EP-A-0 387 930). The individual zones of an empty bottle and in particular of the base of the bottle are examined separately. By the method according to the invention, the reliability of a testing apparatus can be tested separately by means of a single test bottle for every type of defect and every recognition zone, as a test bottle can have a certain reference value for every type of defect and every recognition zone. The number of test bottles can thereby be greatly reduced.

A test bottle can e.g. have a defect in the mouth zone and a defect in every individual zone of the side wall recognition, e.g. represented by a rod standing in the centre of the bottle, and in each case a defect in the base zone in the various recognition zones, namely edge zone, transition, edge middle and base middle. The defects in the side wall and the base zones can be made from opaque insulating tape and correspond to a defined reference value. Additionally, defects in the form of transparent foreign bodies e.g. from cellophane, can be provided for the side wall and the base, in order to also test the reliability of the testing apparatus with regard to transparent foreign bodies.

A separate test bottle is however generally used to test the reliability of a testing apparatus which detects caustic solution residues in empty bottles. Caustic solutions are polar liquids, so that they conduct high-frequency electric radiation better than air. Caustic solution residues can therefore be recognised by ascertaining the absorption of high-frequency electromagnetic radiation. The feature signal is a measure of the lesser absorption of the electromagnetic radiation, which it experiences through the caustic solution residues. If the intensity of the electromagnetic radiation let through by an empty bottle exceeds a threshold value, the first condition is no longer fulfilled and the empty bottle concerned is eliminated as defective from further production steps. The test bottle receives a certain amount of the caustic washing solution, and the corresponding feature signal is entered in the test apparatus as a reference value. when testing the reliability of the residual caustic solutions test apparatus, the feature signal for the test bottle must correspond to the reference value with minor deviations. At the same time, the residual caustic solutions test is an example of how the method according to the invention can also be used with analogue feature signals.

A further example is the determination of liquid remains on the base of the bottle by measuring the resulting attenuation of IR light. Caustic solution residues in an empty bottle are recognized both in the preceding special test for caustic solution residues and the general determination of liquid residues by means of IR attenuation. Certain features of objects can thus also be tested in two different ways.

The method according to the invention can also be used to test the reliability of testing apparatus which work with different initial variables as feature signal. Examples are systems for recognizing light or dark pixels or systems for evaluating brightness distributions, (histograms), which, considered for themselves or after evaluation via arithmetic algorithms, represent parameters for the quality of bottles or other objects.

DETAILED DESCRIPTION OF THE INVENTION

Figure 1:
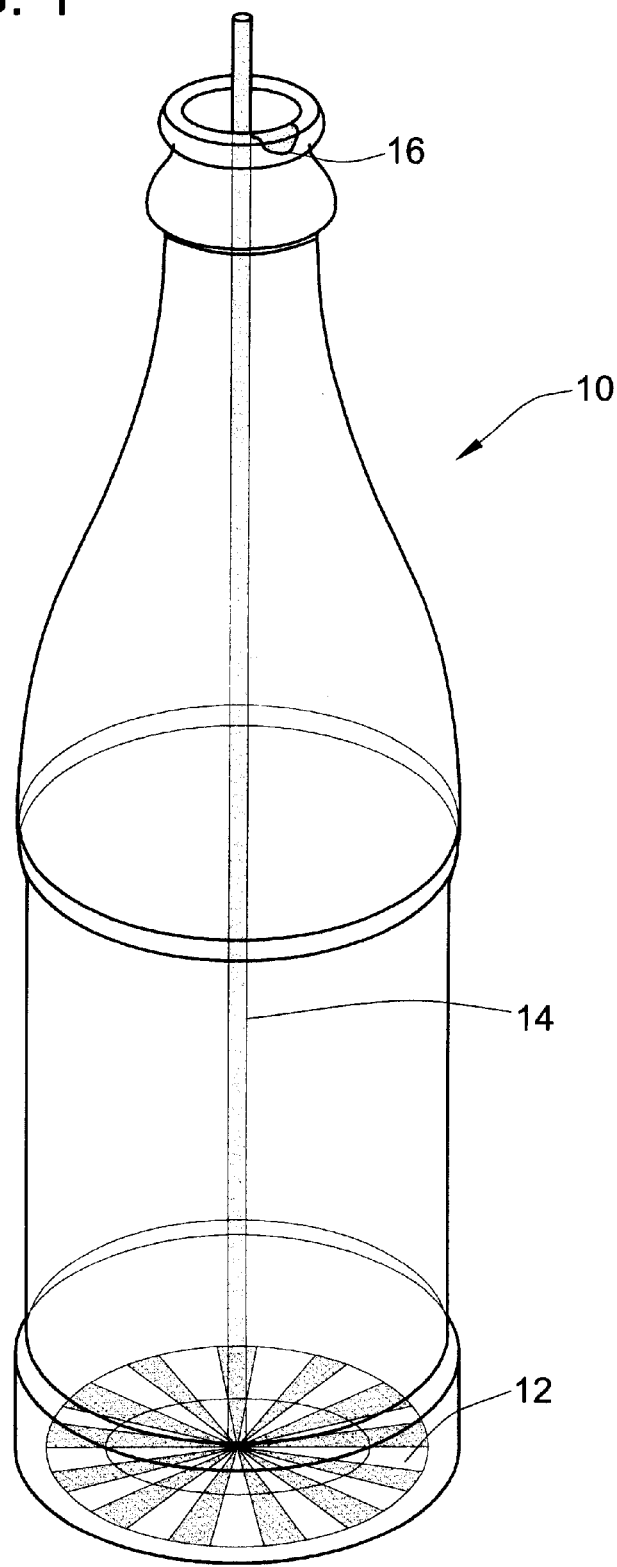
FIG. 1 is a perspective view of a test bottle having a radial pattern at its base, and a rod inserted therein for performing a testing method in accordance with teachings of the present invention.

The attached Figure shows a test bottle, which is recognised as defective both during side wall recognition and during base recognition and the mouth test i.e. does not fulfil the corresponding first conditions. The bottle 10 is a normal 0.7–1 water bottle made from glass. On the base the test bottle 10 has a radial pattern 12, which generates a very high number of light-dark transitions during base recognition. Arranged axially in the middle is a rod 14, which always creates the same number of light-dark transitions irrespective of the rotation position of the test bottle 10. Finally, the test bottle 10 also has a splinter 16 on the opening edge. The purpose of this splinter is to test the reliability of the testing apparatus which monitors the mouth of the empty bottle by means of image evaluation facility. The image evaluation facility comprises an outer annular recognition zone which corresponds to the outwardly dropping zone of the mouth, as well as an adjoining inner annular recognition zone which corresponds to the horizontal zone of the mouth. The splinter 16 leads in the outer recognition zone to a decrease in the number of light-dark transitions, while it leads to an increase in the number of light-dark transitions in the inner recognition zone.

Such a test bottle is guided through the testing apparatus together with the stream of empty bottles by the method according to the invention. The test bottle must be recognisable as such, in order that the observance of the second condition, i.e. the agreement with the set or read-in reference value can be checked in the testing apparatus. To this end, the test bottle has a mark, e.g. a metal ring or a ring made of triple-reflex foil, so that it can be recognised as a test bottle by the testing apparatus by means of a suitable recognition device, e.g. metal detector or a light barrier. An identification of the test bottle can however also be recognised by the control device of the testing apparatus, through software, by the large number of defects occurring in this bottle. It would be highly unlikely for such a large number of defects to occur in a normal empty bottle. If, therefore, the occurrence of all these defects is recognised in a single empty bottle in an order of magnitude that is typical for the test bottle, then it can be concluded that it is a test bottle and the observance of the second condition can be checked.

In the simultaneously filed patent application entitled "Method for determining parameters, e.g. fill level, pressure or gas composition, in closed containers" (in-house reference: 31458/Füllstandsk., corresponds to DE 196 46 685.7), a method is described for determining the fill level of liquids in containers which are sealed by a cap, the cap being excited by a short magnetic pulse to perform primary mechanical vibrations. The secondary vibrations excited by the primary mechanical vibrations of the cap in the container, which take place within the space between the cap and the liquid, are recorded by means of a microphone and are analysed, the fill level being ascertained from the established frequency of these secondary vibrations. The internal pressure of the container can additionally be deduced from an analysis of the primary mechanical vibrations. The method according to the invention can also be used on this occasion. The feature signal is on this occasion the frequency of the secondary vibrations for the fill level. The first condition is that this frequency lies above a certain value, e.g. 7 kHz; smaller frequencies mean too large an air space in the neck of the bottle and thus too low a fill level. The second condition, which is characteristic for the correct operation of the testing apparatus, is that the feature signal for the test bottle corresponds to the set reference value which was previously entered for the test bottle.

A further possible way of testing the reliability of a testing apparatus and in particular the cleanness of the optical recognition system results when checking the wall contrast during side wall recognition. The contrast difference, i.e. the brightness difference of the edge of the bottle, which appears black due to the strong refraction of the light beams penetrating it, is determined in relation to the background lighting or to the brightness of the centre of the bottle. Deviations from the average of this brightness difference allow a very early statement about a deterioration in recognition efficiency and thus in the reliability of the testing apparatus.

The sensitivity of the testing apparatus can be automatically tracked in a certain zone by means of the previously described versions of the method according to the invention. In the case of relatively small deviations of the feature signal from the reference value, e.g. a deviation of 5%, the threshold values or limit values, which are decisive when testing the first condition, can be changed by a corresponding percentage. Only when the deviation is larger than e.g. 5% is a warning signal given and, when a further threshold value for the deviation, e.g. of 20%, is exceeded, the testing apparatus is stopped, because there is no longer a certainty of recognition of specific defects. However, if the permitted deviation is established, the original read-in reference value is used in each case.

What is claimed is:

1. A method for testing the reliability of an apparatus which checks a large number of empty bottles of the same type made of transparent material for freedom from defects and the absence of foreign bodies the method comprising:

scanning an image of each empty bottle pointwise by means of a recognition apparatus;

generating a feature signal for each empty bottle, which is based on brightness distribution (histogram);

comparing the feature signal with a threshold value;

conducting a test bottle to the checking apparatus after a number of empty bottles;

checking the feature signal of the test bottle to determine if the feature signal of the test bottle corresponds to a pre-set reference value; and wherein the feature signal contains details of the distribution of the light-dark contrasts and similarly the reference value contains details of the contrast distribution of the light-dark distributions and when the feature signal of the test bottle is checked, it is also checked if the details of the contrast distribution contained in the feature signal correspond to those of the reference value.

* * * * *